United States Patent [19]

Bouillon et al.

[11] 4,323,553
[45] Apr. 6, 1982

[54] COMPOSITION FOR STRENGTHENING AND REVITALIZING BRITTLE OR DAMAGED NAILS CONTAINING A SALT OF 2-BENZYLTHIO ETHYLAMINE

[75] Inventors: Claude Bouillon, Eaubonne; Patrick Darmenton, Villejuif, both of France

[73] Assignee: L'Oreal, Paris, France

[21] Appl. No.: 144,872

[22] Filed: Apr. 29, 1980

[30] Foreign Application Priority Data

May 3, 1979 [FR] France .................................. 79 11115

[51] Int. Cl.³ ................................................ A61K 7/04
[52] U.S. Cl. ..................................... 424/61; 424/358; 424/365
[58] Field of Search .......................... 424/61, 358, 365

[56] References Cited

FOREIGN PATENT DOCUMENTS

| 1617705 | 4/1972 | Fed. Rep. of Germany | 424/70 |
| 3111M | 2/1965 | France | 424/70 |
| 2002461 | 10/1969 | France | 424/70 |
| 2011940 | 3/1970 | France | 424/70 |
| 2042569 | 2/1971 | France | 424/70 |
| 2155776 | 10/1971 | France | 424/70 |

Primary Examiner—Anna P. Fagelson

[57] ABSTRACT

A composition for strengthening and revitalizing brittle or damaged nails comprises in a cosmetic vehicle for application to the nail an effective amount of a salt of a mineral or organic acid of 2-benzylthio ethylamine.

8 Claims, No Drawings

COMPOSITION FOR STRENGTHENING AND REVITALIZING BRITTLE OR DAMAGED NAILS CONTAINING A SALT OF 2-BENZYLTHIO ETHYLAMINE

The present invention relates to the use of certain active compounds for strengthening and revitalizing brittle or damaged nails, and, principally, nails having a tendency to crack or split.

It is well known that nails, in particular women's nails, frequently exhibit structural and stability defects. These defects are of very diverse origin and are principally attributable to the internal functioning of the individual, to the person's lifestyle, eating habits, age or state of fatigue or overexertion. These defects can also be the result of an erosive action, caused for example by prolonged exposure and/or repeated exposure to detergent agents, to solvents and to household chemical products.

These structural and stability defects can thus render the surface of the nails unattractive, which can be upsetting or disconcerting to the individual. These defects can also cause certain physical unpleasantness ranging from inconvenience to irritation and even to actual pain.

With the view of treating nails, so as to strengthen and revitalize them, it has previously been proposed to use various types of compositions based on certain active products.

These known compositions are essentially based on either formol or N-methylolated derivatives, or on cysteine derivatives and principally S-carboxymethyl cysteine.

The use of nail hardening compositions based on formol so as to exert a crosslinking action of the proteins involves certain risks due to the potential reactivity of formol vis-a-vis the skin. Thus the use of such compositions, which is generally considered unacceptable, runs the risk causing sensitization of the skin and all the more so since, in this type of composition, it is necessary to use a relatively high concentration of formol in order to obtain satisfactory results.

Compositions based on S-carboxymethyl cysteine act trophically on the nail by furnishing to it from the cysteine one of the eighteen amino acids which enter into the polypeptide chain of the keratinic nail structure.

However, even though certain results can be achieved with this type of composition, nonetheless, the results are not totally satisfactory, chiefly with regard to strengthening nails having a tendency to split.

After numerous tests with various classes of sulfur compounds, it has now been ascertained that not only can the above disadvantages of known compositions be avoided, but also excellent results can be obtained in the strengthening and revitalization of fragile or damaged nails, by using in an appropriate composition certain organic sulfur compounds which, until now, have never been contemplated in this type of composition.

In effect, after numerous tests on women's brittle or damaged nails, it has been established that the nails can be significantly strengthened and a more healthy appearance imparted thereto by using certain salts of 2-benzylthio ethylamine.

The present invention thus relates to the use, for the strengthening and revitalizing brittle or damaged nails, at least one salt of a mineral or organic acid of 2-benzylthio ethylamine of the formula $$C_6H_5-CH_2-S-CH_2-CH_2-NH_2 \qquad (I)$$

The said mineral acid is, preferably, hydrochloric acid, hydrobromic acid or phosphoric acid and the said organic acid is, preferably, malic acid, tartaric acid, salicylic acid, succinic acid, aspartic acid, glutamic acid, maleic acid, fumaric acid or 5-amino-3-thia hexanedioic acid.

These active compounds, used in accordance with the present invention, are known and have already been described in several literature articles including certain prior patents of the present assignee.

Representative compounds, corresponding to formula I above, which can advantageously be used in accordance with the invention include, in particular, the 2-benzylthio ethylamine hydrochloride, 2-benzylthio ethylammonium malate, 2-benzylthio ethylammonium tartrate, 2-benzylthio ethylammonium aspartate, 2-benzylthio ethylammonium glutamate and the 5-amino-3-thia hexanedioate of 2-benzylthio ethylammonium.

The active compounds, such as defined above, are generally used in admixture in an appropriate cosmetic vehicle for application to the nail and are present in an amount between 0.05 and 5 weight percent, preferably between 0.2 and 2 weight percent thereof.

The compositions of the present invention which include these active compounds are provided, preferably, in the form of water-in-oil or oil-in-water emulsions.

When the emulsion is an oil-in-water type emulsion, it contains, preferably:

from 2–14 weight percent of a polyoxyethylene ester and, particularly, polyoxyethene stearate, from 0.5 to 3 weight percent of a glyceryl ester and, principally, glyceryl mono- and di-stearate, and from 2 to 9 weight percent of a fatty alcohol, principally, cetyl alcohol.

These compositions in the form of an oil-in-water emulsion can also contain up to 20 weight percent isopropyl palmitate, up to 20 weight percent ethyldiglycol, and up to 7 weight percent of an oil such as petrolatum oil, silicone oil or a vegetable oil. These emulsions can also contain from 1 to 20 weight percent of hydrogenated palmetto oil or from 0.2 and 0.5 weight percent of a polymethacrylic acid such as that sold under the commercial name of CARBOPOL by Goodrich.

When the emulsion is a water-in-oil type emulsion, it contains, preferably:

from 2 to 40 weight percent of paraffin oil, from 2 to 30 weight percent of glycerine, and from 1 to 40 weight percent of a mixture of paraffinic hydrocarbons, of mono- and di-glycerides, of aliphatic alcohols and of sterols, and, in particular, the mixture sold under the commercial name of "Protegin X" Goldschmidt.

This "Protegin X" product has the following composition:

| | |
|---|---|
| Paraffinic hydrocarbons of partially microcrystalline structure | about 53% |
| Partial ester of fatty acids and glycerol | about 25% |
| Aliphatic alcohols | about 5% |
| Terpenes | about 10% |
| Steroids | about 7% |

These water-in-oil type emulsions can also contain magnesium sulfate (hydrated) in an amount between 0.1 and 3 weight percent.

Although the emulsions constitute the preferred form of the compositions according to the present invention, the composition can also be provided in the form of a hydroalcoholic solution in which the amount of alcohol (ethanol or isopropanol) is between 10 and 70 weight percent.

In accordance with this embodiment of the invention, the composition also contains, preferably, from 0.5 to 5 weight percent of at least one compound of the formula

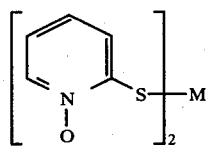

(II)

wherein M represents either a covalent bond and the compound can be provided in the form of a complex, or the divalent residue of the formula $>Al-OSO_3R$ wherein R represents alkyl having 1-4 carbon atoms, β-aminoethyl, 2-amino-2-carboxy ethyl, phenyl, phenyl substituted by alkyl having 1-3 carbon atoms, hydroxy or halogen, or R represents 2-oxo-10 bornanyl.

When, in the compound of formula II above, M represents a covalent bond, that is to say, corresponds to 2,2'-dithio bis (pyridine N-oxide), this compound can be used, in accordance with the invention, in the form of a complex with a metallic salt, such as, for example, the calcium chloride or the magnesium sulfate complex. Such complexes are described in U.S. Pat. No. 3,818,018 (French patent application No. 72.36766).

Representative compounds of formula II that can be used in accordance with the present invention include 2,2'-dithio bis (pyridine N-oxide), bis (2N-oxypyridyl)aluminum camphosulfate, bis (2-N-oxypyridyl) aluminum p-toluene sulfonate, bis (2-N-oxypyridyl) aluminum methane sulfonate, bis (2N-oxypyridyl) aluminum β-amino ethane sulfonate and bis (2-N-oxypyridyl) aluminum 2-amino-2-carboxy ethane sulfonate.

However, the compositions, be they provided in the form of emulsions or hydroalcoholic solutions, can also contain in admixture various other types of components and, in particular, sorbitol, propyleneglycol, poilyethylene glycol having a molecular weight between 200 and 1500, an antioxidant, a dye, a pigment, a preservative, a non-saponifiable extract of a vegetable oil, a perfume, a soluble protein such as gelatin, collagen or soluble keratin, an aminated acid, a protein hydrolyzate and/or a vitamin such as A, $D_3$, E, F, B and C.

The present invention also relates to a process for strengthening the nails comprising applying on a regular basis to the surface of the nail with the aid of a brush an effective amount of a composition such as defined above.

To obtain a lasting effect, it is recommended that the composition be applied daily and preferably in the evening so that the desired action of the composition on the nail can take place during the night.

After the above composition has dried on the nail, a colorless or colored nail enamel can be applied thereover, the adhesion of the enamel film to the nail being excellent.

The following non-limiting examples are given to illustrate the present invention.

EXAMPLES OF COMPOSITIONS

A. Oil-in-water Emulsions

Example 1

| | |
|---|---|
| Polyoxyethylene stearate with 20 moles of ethylene oxide | 3 g |
| Glycerol mono- and di-stearate | 0.6 g |
| Cetyl alcohol | 2 g |
| Corn germ oil | 7 g |
| Petrolatum oil | 8 g |
| Carbopol | 0.2 g |
| Triethanol amine, sufficient amount for | pH 6 |
| 2-benzylthio ethylammonium malate | 2 g |
| Water, sufficient amount for | 100 g |

With daily application of this emulsion there is noted after a few weeks a remarkable improvement in the general state of the brittle nails.

Example 2

| | |
|---|---|
| Polyoxyethylene stearate with 20 moles of ethylene oxide | 8.25 g |
| Glycerol mono- and di-stearate | 1.5 g |
| Cetyl alcohol | 5.25 g |
| Isopropyl palmitate | 4 g |
| Interesterified hydrogenated palmetto oil | 5 g |
| Ethyl diglycol | 5 g |
| Bis (2-N-oxypyridyl) aluminum camphosulfonate | 0.1 g |
| 2-benzylthio ethylammonium malate | 1.5 g |
| Perfume | 0.2 g |
| Water, sufficient amount for | 100 g |

Example 3

| | |
|---|---|
| Polyoxyethylene stearate with 20 moles of ethylene oxide | 6 g |
| Glycerol mono- and di-stearate | 1.2 g |
| Cetyl alcohol | 4 g |
| Sunflower oil | 5 g |
| Silicone oil | 4 g |
| Palmetto oil | 3 g |
| 2-benzylthio ethylammonium aspartate | 2 g |
| Preservative | 0.3 g |
| Water, sufficient amount for | 100 g |

Example 4

| | |
|---|---|
| Polyoxyethylene stearate with 20 moles of ethylene oxide | 3 g |
| Glycerol mono- and di-stearate | 0.6 g |
| Cetyl alcohol | 2 g |
| Sunflower oil | 7 g |
| Petrolatum oil | 8 g |
| Carbopol | 0.2 g |
| Triethanolamine, sufficient amount for | pH 6 |
| 5-amino-3-thia hexanedioate of 2-benzylthio ethylammonium | 2.5 g |
| Pyridoxine camphosulfonate | 0.9 g |
| Preservative | 0.2 g |
| Perfume | 0.3 g |
| Water, sufficient amount for | 100 g |

Example 5

| | |
|---|---|
| Polyoxyethylene stearate with 20 moles of ethylene oxide | 8.25 g |
| Glycerol mono- and di-stearate | 1.5 g |
| Cetyl alcohol | 5.25 g |
| Isopropyl palmitate | 4 g |
| Interesterified hydrogenated palmetto oil | 5 g |
| Ethyl diglycol | 5 g |
| Preservative | 0.3 g |
| 2-benzylthio ethylammonium malate | 5 g |
| Perfume | 0.3 g |
| Water, sufficient amount for | 100 g |

B. Water-in-oil emulsions

Example 6

| | |
|---|---|
| Protegin X | 20 g |
| Paraffin oil | 10 g |
| Glycerol | 5 g |
| Hydrated magnesium sulfate | 0.5 g |
| 2-benzylthio ethylammonium malate | 2 g |
| Water, sufficient amount for | 100 g |

Example 7

| | |
|---|---|
| Protegin X | 10 g |
| Paraffin oil | 20 g |
| Glycerol | 10 g |
| Magnesium sulfate | 2 g |
| 2-benzylthio ethylammonium tartrate | 1.5 g |
| Non-saponifiables of soy bean oil | 0.2 g |
| Water, sufficient amount for | 100 g |

Example 8

| | |
|---|---|
| Protegin X | 30 g |
| Paraffin oil | 5 g |
| Glycerol | 5 g |
| Magnesium sulfate | 1 g |
| 2-benzylthio ethylammonium glutamate | 3 g |
| Water, sufficient amount for | 100 g |

Example 9

| | |
|---|---|
| Protegin X | 20 g |
| Paraffin oil | 10 g |
| Glycerol | 5 g |
| Magnesium sulfate | 0.5 g |
| 5-amino-3-thia hexanedioate of 2-benzylthio ethylammonium | 2 g |
| Vitamin A $D_3$E-Biotin | 0.1 g |
| Water, sufficient amount for | 100 g |

Example 10

| | |
|---|---|
| Protegin X | 20 g |
| Paraffin oil | 10 g |
| Glycerol | 5 g |
| Magnesium sulfate complex of 2,2'-dithio bis (pyridine N-oxide) | 0.1 g |
| 2-benzylthio ethylammonium malate | 1.8 g |
| Vitamin F | 0.8 g |
| Vitamin A $D_3$E-Biotin | 0.1 g |
| Water, sufficient amount for | 100 g |

C. Hydroalcoholic solution

Example 11

| | |
|---|---|
| 2-benzylthio ethylammonium malate | 2 g |
| Bis-(2-N-oxypyridyl) aluminum camphosulfonate | 0.05 g |
| Polyethylene glycol 600 | 2 g |
| Sorbitol | 4 g |
| Vitamin F | 0.8 g |
| Nonsaponifiables of alfalfa | 0.2 g |
| Perfume | 0.3 g |
| Ethanol at 70°, sufficient amount for | 100 g |

Example 12

| | |
|---|---|
| 5-amino-3-thia hexanedioate of 2-benzylthio ethylammonium | 2 g |
| Magnesium sulfate complex of 2,2'-dithio bis (pyridine N-oxide) | 0.15 g |
| Soluble keratin | 0.5 g |
| Vitamin A $D_3$E-Biotin | 0.1 g |
| Perfume | 0.2 g |
| Ethanol | 15 g |
| Water, sufficient amount for | 100 g |

Example 13

| | |
|---|---|
| 2-benzylthio ethylammonium tartrate | 1.2 g |
| 2,2'-dithio bis (pyridine N-oxide) | 0.5 g |
| Soluble collagen | 0.2 g |
| Polyethylene glycol 400 | 3 g |
| Ethanol or isopropanol | 30 g |
| Perfume | 0.4 g |
| Water, sufficient amount for | 100 g |

Example 14

| | |
|---|---|
| 2-benzylthio ethylammonium malate | 4 g |
| 2,2'-dithio bis (pyridine N-oxide) | 0.3 g |
| Propylene glycol | 6 g |
| Polyethylene glycol 1500 | 1 g |
| Vitamin F | 0.8 g |
| Butyl hydroxy anisole | 0.1 g |
| Butyl hydroxy toluene | 0.1 g |
| Perfume | 0.5 g |
| Ethanol | 45 g |
| Water, sufficient amount for | 100 g |

Example 15

| | |
|---|---|
| 2-benzylthio ethylammonium aspartate | 0.8 g |
| Bis(2-N-oxypyridyl) aluminum camphosulfonate | 0.2 g |
| Polyethylene glycol 300 | 1.5 g |
| Glycerol | 4 g |
| Perfume | 0.15 g |
| Ethanol | 40 g |
| Water, sufficient amount for | 100 g |

Example 16

| | |
|---|---|
| 2-benzylthio ethylamine hydrochloride | 1 g |
| Calcium chloride complex of 2,2'-dithio bis (pyridine N-oxide) | 0.2 g |
| Soluble keratin | 0.5 g |
| Vitamin A D$_3$E-Biotin | 0.1 g |
| Perfume | 0.2 g |
| Ethanol | 15 g |
| Water, sufficient amount for | 100 g |

What is claimed is:

1. A process for strengthening and revitalizing brittle or damaged nails comprising applying to the surface of the nails an effective amount of a composition comprising in a cosmetic vehicle from 0.05 to 5 weight percent of a mineral or organic acid salt of 2-benzylthio ethylamine having the formula $$C_6H_5-CH_2-S-CH_2-CH_2NH_2.$$

2. The process of claim 1 wherein said mineral or organic acid salt is selected from the group consisting of 2-benzylthio ethylamine hydrochloride, 2-benzylthio ethylammonium malate, 2-benzylthio ethylammonium tartrate, 2-benzylthio ethylammonium aspartate, 2-benzylthio ethylammonium glutamate and the 5-amino-3 thia hexanedioate of 2-benzylthio ethylammonium.

3. The process of claim 1 wherein said mineral or organic acid salt is present in said composition in an amount from 0.2 to 2 weight percent thereof.

4. The process of claim 1 wherein said cosmetic vehicle is an oil-in-water emulsion containing from 2–14 weight percent of a polyoxyethylene ester, from 0.5 to 3 weight percent of a glyceryl ester, and from 2 to 9 weight percent of a fatty alcohol.

5. The process of claim 1 wherein said cosmetic vehicle is a water-in-oil emulsion containing from 2 to 40 weight percent of paraffin oil, from 2 to 30 weight percent of glycerine, and from 1 to 40 weight percent of a mixture of paraffinic hydrocarbons, mono- and diglycerides, an aliphatic alcohol and a sterol.

6. The process of claim 5 wherein said cosmetic vehicle also contains from 0.1 to 3 weight percent of magnesium sulfate.

7. The process of claim 1 wherein said cosmetic vehicle is a hydroalcoholic solution wherein the alcohol is present in an amount between 10 and 70 weight percent.

8. The process of claim 1 wherein said composition also contains from 0.5 to 5 weight percent of a compound having the formula:

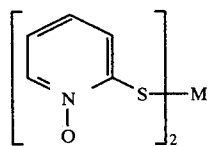

wherein M represents either (1) a covalent bond and the compound is provided in the form of a complex, or (2) a divalent residue of the formula, $>$Al—OSO$_3$R wherein R represents alkyl having 1–4 carbon atoms, β-aminoethyl, 2-amino-2-carboxy ethyl, 2-oxo-10 bornanyl, phenyl or phenyl substituted by (i) alkyl having 1–3 carbon atoms, (ii) hydroxy or (iii) halogen.

* * * * *